US012592137B2

(12) United States Patent
Munuera

(10) Patent No.: US 12,592,137 B2
(45) Date of Patent: Mar. 31, 2026

(54) CONDENSATION MONITORING IN ASPIRATING SMOKE DETECTION SYSTEMS

(71) Applicant: KIDDE FIRE PROTECTION, LLC, Bradenton, FL (US)

(72) Inventor: Jose Manuel Munuera, Barcelona (ES)

(73) Assignee: KIDDE FIRE PROTECTION, LLC, Bradenton, FL (US)

( * ) Notice: Subject to any disclaimer, the term of this patent is extended or adjusted under 35 U.S.C. 154(b) by 212 days.

(21) Appl. No.: 18/319,208

(22) Filed: May 17, 2023

(65) Prior Publication Data

US 2024/0029532 A1     Jan. 25, 2024

(51) Int. Cl.
| | |
|---|---|
| *G08B 17/117* | (2006.01) |
| *G01N 1/22* | (2006.01) |
| *G01N 1/24* | (2006.01) |
| *G01N 33/00* | (2006.01) |
| *G08B 29/20* | (2006.01) |

(52) U.S. Cl.
CPC ......... *G08B 17/117* (2013.01); *G01N 1/2205* (2013.01); *G01N 1/2273* (2013.01); *G01N 1/24* (2013.01); *G01N 33/0011* (2013.01); *G08B 29/20* (2013.01)

(58) Field of Classification Search
CPC .... G08B 17/117; G08B 29/20; G01N 1/2273; G01N 1/24; G01N 33/0011; G01N 1/2205
USPC ........................................................ 73/31.02
See application file for complete search history.

(56) References Cited

U.S. PATENT DOCUMENTS

| | | | |
|---|---|---|---|
| 7,768,412 B2 | 8/2010 | Vokey | |
| 10,598,646 B1 * | 3/2020 | Horning | ............. G01N 33/0036 |

(Continued)

FOREIGN PATENT DOCUMENTS

| | | |
|---|---|---|
| CN | 106781202 A | 5/2017 |
| CN | 106846706 A | 6/2017 |

(Continued)

OTHER PUBLICATIONS

Extended European Search Report received for EP Application No. 22382478.0, mailed on Nov. 8, 2022, 12 Pages.

*Primary Examiner* — Stephanie E Bloss
*Assistant Examiner* — Kevin C Butler
(74) *Attorney, Agent, or Firm* — CANTOR COLBURN LLP

(57) ABSTRACT

The aspirating detection system (1) comprises: a central detection unit (7) configured to analyse sample air from the monitored environment (100); a sampling pipe (5) for providing the sample air to the central detection unit (7) from the monitored environment (100), wherein the central detection unit (7) is configured to draw the sample air along the sampling pipe (5); at least one ambient temperature sensor (110a, 110c, 110d) configured to sense an ambient temperature value corresponding to an ambient temperature outside of the aspirating detection system (1); at least one sample air temperature sensor (100b, 100c, 110d) configured to sense a sample air temperature value corresponding to a temperature of the sample air; and a controller (105) configured to determine a condensation occurrence condition is met when a difference between the sample air temperature value and a corresponding ambient air temperature value exceeds a condensation threshold value.

13 Claims, 2 Drawing Sheets

(56) References Cited

U.S. PATENT DOCUMENTS

| | | | | |
|---|---|---|---|---|
| 11,711,871 | B2 * | 7/2023 | Patel | H05B 3/845 |
| | | | | 236/44 C |
| 2005/0089076 | A1 * | 4/2005 | Lindstrom | G01N 25/66 |
| | | | | 348/E5.09 |
| 2011/0146965 | A1 * | 6/2011 | Gloeckner | F24F 11/523 |
| | | | | 165/230 |
| 2022/0190563 | A1 * | 6/2022 | Hilker | G08B 21/182 |
| 2023/0007739 | A1 * | 1/2023 | Patel | H05B 3/845 |
| 2024/0029532 | A1 * | 1/2024 | Munuera | G08B 29/18 |
| 2024/0219055 | A1 * | 7/2024 | Wang | F24F 11/63 |

FOREIGN PATENT DOCUMENTS

| | | | | | |
|---|---|---|---|---|---|
| CN | 108734917 | A | | 11/2018 | |
| CN | 111540158 | A | | 8/2020 | |
| CN | 111540159 | A | | 8/2020 | |
| CN | 111564019 | A | | 8/2020 | |
| CN | 111627182 | A | | 9/2020 | |
| CN | 112053531 | A | * | 12/2020 | |
| CN | 112233361 | A | | 1/2021 | |
| CN | 112233363 | A | | 1/2021 | |
| CN | 112233365 | A | | 1/2021 | |
| CN | 112750287 | A | | 5/2021 | |
| CN | 118043604 | A | * | 5/2024 | F24F 11/38 |
| EP | 0615218 | B1 | | 9/1996 | |
| EP | 0838794 | B1 | | 12/2003 | |
| EP | 1638062 | A1 | * | 3/2006 | G08B 17/10 |
| EP | 1596349 | B1 | | 7/2006 | |
| EP | 1638062 | B1 | | 6/2008 | |
| EP | 1889238 | B1 | | 8/2009 | |
| EP | 1540615 | B1 | | 7/2012 | |
| EP | 2172916 | B1 | | 12/2012 | |
| EP | 2603907 | B1 | | 10/2014 | |
| EP | 2601644 | B1 | | 3/2015 | |
| EP | 3028076 | B1 | | 7/2019 | |
| EP | 2959465 | B1 | | 4/2020 | |
| EP | 3907714 | A1 | | 11/2021 | |
| EP | 4280189 | A1 | * | 11/2023 | G08B 17/10 |
| JP | 2005250986 | A | | 9/2005 | |
| JP | 2007299354 | A | * | 11/2007 | |
| KR | 101860267 | B1 | * | 5/2018 | A62C 3/00 |
| KR | 102123737 | B1 | | 6/2020 | |
| KR | 102152657 | B1 | | 9/2020 | |
| KR | 102322584 | B1 | * | 11/2021 | |
| KR | 102643837 | B1 | * | 3/2024 | F25D 13/00 |
| WO | 2021237502 | A1 | | 12/2021 | |

* cited by examiner

CONDENSATION MONITORING IN ASPIRATING SMOKE DETECTION SYSTEMS

CROSS REFERENCE TO RELATED APPLICATIONS

This application claims priority to European Patent Application No. 22382478.0 filed on May 18, 2022.

TECHNICAL FIELD

The present invention relates to monitoring condensation in an aspirating detection system.

BACKGROUND

Aspirating detection systems are systems which actively draw air from various sampling locations to a centralised detection location (i.e. a central detection unit) via a network of pipes. The sample air drawn from the sampling locations is then analysed to determine if one or more target substances are present in the one or more sampling locations. Accordingly, it is understood that an aspirating detection system generally comprises a central detection unit, and one or more pipes through which air is aspirated to the central detection unit.

Aspirating detection systems are often implemented as aspirating smoke detectors, i.e. aspirating detection systems employed for smoke detection. Aspirating smoke detection systems are used in buildings or other locations where point smoke detectors are not appropriate, for example due to inaccessibility or a need for invisible smoke detection. Once smoke is detected the aspirating smoke detector generates an alarm, indicating that the sampling location, i.e. the monitored environment, is compromised. By using a centralised detection location, aspirating detection systems may sample large areas (e.g. entire and/or multiple floors and rooms of buildings or other structures) with high efficiency and/or accuracy.

The aspiration of air from the one or more sampling locations can lead to an occurrence of condensation in and/or around parts of the aspirating detection system when warm, moist air is adjacent cool parts of the aspirating detection system. For example, cool sampling air may cause condensation on the outside of the pipes in warm ambient conditions, or warm sampling air may cause condensation inside of the pipes in cold ambient conditions. Condensed water droplets can also freeze if they form in a sufficiently cold environment, leading to a build-up of ice in and/or around the aspirating detection system.

Condensation is particularly prevalent in climate-controlled, or thermally regulated, monitored environments. The occurrence of condensation can reduce the reliability or functionality of the aspirating detection system.

It is desirable to provide an aspirating detection system which may more reliably monitor a climate-controlled environment.

SUMMARY

Viewed from a first aspect of the present invention, there is provided an aspirating detection system for monitoring an environment. The aspirating detection system comprises: a central detection unit configured to analyse sample air from the monitored environment; a sampling pipe for providing the sample air to the central detection unit from the monitored environment, wherein the central detection unit is configured to draw the sample air along the sampling pipe; at least one sample air temperature sensor configured to sense an ambient temperature value corresponding to an ambient temperature outside of the aspirating detection system; at least one sample air temperature sensor configured to sense a sample air temperature value corresponding to a temperature of the sample air; and a controller configured to determine a condensation occurrence condition is met when a difference between the sample air temperature value and a corresponding ambient temperature value exceeds a condensation threshold value.

By determining if the condensation occurrence condition is met, the aspirating detection system is capable of monitoring for the likely occurrence of condensation in and/or around the aspirating detection system. Accordingly, the aspirating detection system may be able to warn against the potential occurrence of condensation, such that suitable action, such as modification or maintenance of the aspirating detection system, may be more reliably taken.

The ambient air temperature sensor may be regarded as an external temperature sensor, as it is configured to sense an ambient temperature corresponding to an ambient temperature external to the aspirating detection system.

The sample air temperature sensor may be regarded as an internal temperature sensor, as it is configured to sense a sample air temperature value corresponding to a temperature of the sample air internal to the sampling pipe.

A single sensor unit may contain both an ambient temperature sensor and a sample air temperature sensor. That is, the aspirating detection system may comprise at least one temperature sensor unit configured to sense both an ambient temperature value corresponding to an ambient temperature value corresponding to an ambient temperature outside of the aspirating detection system, and a sample air temperature value corresponding to a temperature of the sample air.

The corresponding ambient temperature value may be regarded as an ambient temperature value corresponding to the sample air temperature used in determining if the condensation occurrence condition is met. Accordingly, the corresponding ambient temperature value may be representative of an ambient temperate in a location proximate to (or closest to) where the sample air temperature value was sensed. In some embodiments, a single ambient temperature value may correspond to two or more sample air temperature values.

The condensation threshold value may be a temperature difference threshold value at which condensation is likely to occur within the aspirating detection system.

In some embodiments, the condensation threshold value may be a fixed value. The condensation threshold value may be estimated, or predetermined, based on a set temperature of the monitored environment and/or an average ambient temperature outside of the aspirating detection system.

In other embodiments, the condensation threshold value may be a variable value. The condensation threshold value may be determined, or estimated, based on a temperature difference between the corresponding ambient temperature value and a dew point value. The controller may be configured to determine and/or dynamically adjust the condensation threshold value periodically.

The dew point value may be estimated based on a humidity outside of the aspirating detection system, or may be based on a sensed humidity value received by the controller. The humidity may be determined using a humidity sensor of the aspirating detection system. Alternatively, the humidity may be determined based on data received from an external system, such as a building HVAC system or the like.

If the condensation occurrence condition is met and the corresponding ambient temperature value is greater than the sample air temperature value, the controller may be configured to determine that condensation is likely to occur on exterior surfaces of the aspirating detection system. If the sample air temperature value is greater than the ambient temperature value, the controller may be configured to determine that condensation is likely to occur on interior surfaces of the aspirating detection system.

The monitored environment is an environment or space the aspirating detection system is arranged to monitor, for example for the purpose of smoke detection or the like.

In some embodiments, the monitored environment is a refrigerated environment. The monitored environment may be maintained at approximately −23° C., e.g. ±5° C. Alternatively, the monitored environment may be maintained at a temperature of less than 0° C.; less than −5° C.; less than −10° C.; less than −15° C.; less than −20° C.; or less than −25° C.

The sampling pipe is at least partially exposed to the monitored environment. In this way, the sampling pipe facilitates flow communication between the monitored environment and the central detection unit.

The central detection unit may be located in a separate environment to the monitored environment. The central detection unit may be regarded as being located in a surrounding environment, i.e. an environment surrounding the central detection unit. The sampling pipe may also be at least partially disposed in the surrounding environment, such that flow communication is facilitated between the monitored environment and the central detection system. The temperature of the surrounding environment may correspond to the ambient temperature outside of the aspirating detection system, for components of the aspirating detection system disposed in the surrounding environment.

The sampling pipe may belong to a network of pipes. The network of pipes may be arranged to facilitate flow communication between a plurality of monitored environments and the central detection unit.

The central detection unit may generally comprise an aspirating device. The aspirating device may be configured to draw the sample air along the sampling pipe.

The central detection unit may also generally comprise a detection device. The detection device may a smoke detection device, or any other device suitable for detecting a desired property or parameter of the sample air, such as a gas sensor.

The at least one ambient temperature sensor may include a first temperature sensor located in a housing of the central detection unit. The first temperature sensor may be located on an internal surface of the central detection unit. Alternatively, the first temperature sensor may be located on an external surface of the central detection unit. The first temperature sensor may thus be disposed to directly sense the ambient temperature around the central detection unit. In some embodiments, this may correspond to the ambient temperature of the surrounding environment.

The at least one sample air temperature sensor may include a second temperature sensor located in a flow path of the sample air through the central detection unit. The second temperature sensor may be thus disposed to directly sense the sample air temperature within the central detection unit.

The first temperature sensor and the second temperature sensor may be separate and/or distinct temperature sensors. That is, the first temperature sensor may comprise a (i.e. first) temperature sensing unit that is different to a (i.e. second) temperature sensing unit of the second temperature sensor.

The ambient temperature value sensed by the first temperature sensor may be the corresponding ambient temperature value to the sample air temperature value sensed by the second temperature sensor. Thus the controller may be regarded as being configured to determine a condensation occurrence condition is met when a difference between the sample air temperature value sensed by the second temperature sensor and an ambient temperature value sensed by the first temperature sensor exceeds a condensation threshold value.

The central detection unit may comprise equipment that is sensitive to the occurrence of condensation, such as a detection device. Accordingly, by being able to monitor for the possible occurrence of condensation in and/or around the central detection unit, a condition or state of operation of the central detection unit may be more reliably determined.

The at least one sample air temperature sensor may include one or more temperature sensors located in a flow path of the sample air along the sampling pipe. Each of the one or more temperature sensors located in the flow path of the sample air along the sampling pipe may be configured to sense a sample air temperature value corresponding to a temperature of the sample air.

The ambient temperature value sensed by the first temperature sensor may be the corresponding ambient temperature value to the sample air temperature values sensed by the one or more temperature sensors located in a flow path of the sample air along the sampling pipe.

The controller may be configured to determine if a condensation occurrence condition is met for each sample air temperature value sensed by the one or more temperature sensors. The determination may be made when a difference between the respective sample air temperature value and the corresponding ambient temperature value exceeds the condensation threshold value. The controller may be configured to determine the possible occurrence of condensation if at least one of the condensation occurrence conditions is met.

The at least one ambient temperature sensor may include the one or more temperature sensors located in a flow path of the sample air along the sampling pipe. That is. the one or more temperature sensors located in a flow path of the sample air along the sampling pipe may be further configured to sense an ambient temperature value corresponding to an ambient temperature outside of the aspirating detection system.

Each of the one or more temperature sensors may comprise at least two temperature sensing portions, sensors or probes configured to respectively measure a sample air temperature and an ambient temperature at the respective location at which the temperature sensor is disposed.

The corresponding ambient temperature value for each of the one or more temperature sensors may thus be the respective ambient temperature value sensed by each of the one or more temperature sensors. Accordingly, the controller may be configured to determine if a condensation occurrence condition is met for each of the one or more temperature sensors, when a difference between the respective sample air temperature value and the respective ambient temperature value exceeds the condensation threshold value. The controller may be configured to determine the possible occurrence of condensation if at least one of these condensation occurrence conditions is met.

As mentioned above, the condensation threshold value may be a variable value based on a temperature difference between the ambient temperature and its dew point. The controller may be configured to determine a respective condensation threshold value for each temperature sensor based on its respective ambient air temperature value.

By determining if a condensation occurrence condition is met for each respective temperature sensor, the aspirating detection system may be able to more reliably monitor for condensation across the aspirating detection system.

Each of the temperature sensors may be in communication with the controller. Each of the temperature sensors may be in wired and/or wireless communication with the controller.

Each of the one or more temperature sensors located in a flow path of the sample air along the sampling pipe may be a wireless temperature sensor. That is, each of the one or more temperature sensors may be configured to be in, or suitable for, wireless communication with the controller.

By providing one or more wireless temperature sensors, the one or more temperature sensors may be easily retrofitted to an existing aspirating detection system, and/or may be more easily placed or moved to a desired location along the sampling pipe to achieve a desired arrangement for monitoring condensation.

The one or more temperature sensors may include a third temperature sensor located along a length of the sampling pipe outside of the monitored environment.

The one or more temperature sensors may include a fourth temperature sensor located along a length of the sampling pipe within the monitored environment.

Under steady-state operating conditions the difference between the sample air temperature and the monitored air temperature may be smaller in the monitored environment, and thus condensation may be less likely to generally occur. However, a larger temperature difference may be experienced along the sampling pipe as the sample air moves from the monitored environment to a different environment and accordingly the occurrence of condensation may be generally more likely downstream of the monitored environment.

However, if under transient conditions e.g. where a door or other opening to the monitored environment is activated and air from another environment rushes in, the operating conditions of the monitored environment may vary. If the monitored environment is a refrigerated environment, an influx of warm air from a surrounding environment may increase the sample air temperature such that condensation may be more likely along a portion of the sampling pipe located in the monitored environment.

Accordingly, in arrangements providing a plurality of temperature sensors configured to sense a sample air temperature and/or an ambient temperature at different locations along the flow path of the sample air, the aspirating detection system may be able to more reliably determine if a condensation occurrence condition is met throughout the aspirating detection system.

The controller may be configured to determine a location of possible condensation occurrence based on a location of where the sample air temperature value was sensed. Each ambient temperature sensor may have an assigned or predetermined location used to determine the location of where the sample air temperature value was sensed.

Each sample air temperature sensor may also have an assigned or predetermine location used to determine the location of where the ambient temperature value was sensed.

For example, if the at least one ambient temperature sensor and the at least one sample air temperature sensor include first and second temperature sensors located in the central detection unit, then at least the location of the second temperature sensor may be used when determining the location of possible condensation occurrence if the condensation occurrence condition is met for the second temperature sensor. Regardless of whether the at least one sample air temperature sensor further includes third and fourth temperature sensors also configured to sense a respective ambient temperature value to which their respective sensed sample air temperature values are compared, or if their respective sensed sample air temperature values are compared to the ambient temperature value of the first temperature sensor, the locations of the third and fourth temperature sensors may be used when determining the location of possible condensation occurrence if the respective condensation occurrence condition is met for the third and fourth temperature sensors.

By determining a location of possible condensation occurrence based on the location of the temperature sensors, specific action may be taken to either maintain and/or modify the aspirating detection system at the respective location. Accordingly, determining the location of the possible condensation occurrence may provide improved monitoring for condensation in aspirating detection systems.

The controller may be configured to generate a signal based on the location of possible condensation occurrence. The signal may comprise a modification signal. The modification signal generally comprises information recommending a user installs one or more condensation mitigation devices at the location of possible condensation occurrence.

The condensation mitigation device may be any form of gravity-based water trap, such as a U-shaped bend or a water collection pipe.

The controller may be configured to generate a warning signal in response to determining that the condensation occurrence condition is met. The warning signal may comprise an alert or information informing a user that condensation is likely occurring. The warning signal may contain an indication of the location of possible condensation occurrence.

The controller may be configured to transmit the warning signal to a monitoring device.

The warning signal may comprise a command to activate a visual and/or aural indicator. The monitoring device may comprise a visual and/or aural indicator, and may be configured to activate the visual and/or aural indicator responsive to receipt of the warning signal.

The controller may be configured to be in communication with the monitoring device. The monitoring device may be a fire control panel, a smartphone, a personal computer or the like. Alternatively, the monitoring device may be integrated with the central detection unit. The monitoring device may comprise a display device for providing a visual display.

The display device may be configured to receive the modification signal.

The display device may be configured to receive the warning signal.

By alerting users when the condensation occurrence condition is met, a user can take action to maintain, or schedule maintenance, of the aspirating detection system.

The controller may be configured to communicate with one or more devices arranged to mitigate the occurrence of condensation in the aspirating detection system.

For example, the controller may be arranged in communication (e.g. wired and/or wireless communication) with the aspirating device of the central detection unit, and may be configured to control a speed of the aspirating device in response to determining that the condensation occurrence condition is met.

If the controller determines that the temperature difference value exceeds the temperature threshold value, the controller may modify a speed of the aspirating device, and preferably decrease a speed of the aspirating device. By decreasing a speed of the aspirating device, the time taken for the sample air to travel from the monitored environment to the central detection unit may increase. Accordingly, the sample air may have more contact time to exchange heat with the sampling pipe and reach an equilibrium temperature with the ambient temperature. This may reduce the occurrence of condensation in the aspirating detection system.

The aspirating detection system may comprise a heater. The heater may be arranged to heat the sample air from the monitored environment, and may be located proximate a boundary of the monitored environment. Accordingly, the heater may be arranged to heat the sample air as it leaves the monitored environment.

The controller may be configured to activate the heater in response to determining that the condensation occurrence condition is met. Accordingly, the heater may heat the sample air from the monitored environment and thereby reduce the temperature difference between the sample air temperature and the ambient temperature. It will be appreciated that the use of a heater may be most effective when the monitored environment is a refrigerated environment. By selectively activating the heater, the sample air is not unnecessarily heated when the condensation risk is low.

Viewed from a second aspect of the present invention, there is provided a method of monitoring for condensation occurrence in an aspirating detection system. The method comprises: sensing an ambient temperature value corresponding to an ambient temperature outside of the aspirating detection system; sensing a sample air temperature value corresponding to a temperature of sample air inside the aspirating detection system; and determining a condensation occurrence condition is met when a difference between the the sample air temperature value and a corresponding ambient temperature value exceeds a condensation threshold value.

By determining if the condensation occurrence condition is met, the method is capable of monitoring for the likely occurrence of condensation in and/or around an aspirating detection system. Accordingly, the method may be able to warn against the potential occurrence of condensation, such that suitable action, such as modification of or maintenance of the aspirating detection system, may be more reliably taken.

The method may comprise determining the condensation threshold value based on a temperature difference between the corresponding ambient temperature value and a corresponding dew point.

The method may comprise sensing a sample air temperature value corresponding to a temperature of sample air inside the aspirating detection system at a plurality of locations. The plurality of locations may be disposed along a flow path of the sample air through the aspirating detection system. The method may comprise determining a condensation occurrence condition is met for each of the plurality of locations. Each determination may be made when a difference between the ambient temperature value and the respective sample air temperature value exceeds a condensation threshold value. In some embodiments, a single ambient temperature value may correspond to two or more sample air temperature values.

The method may comprise sensing an ambient temperature value corresponding to an ambient temperature outside of the aspirating detection system at the plurality of locations. The method may thus comprise determining a condensation occurrence condition is met for each of the plurality of locations when a difference between the corresponding (i.e. respective) ambient temperature value and the respective sample air temperature value exceeds a condensation threshold value.

The method may comprise determining a location of possible condensation occurrence based on a location of where the sample air temperature value was sensed.

The method may comprise generating a signal based on the location of possible condensation occurrence. The signal may be a modification signal. The method may comprise transmitting the modification signal to a monitoring device.

The method may comprise generating a warning signal in response to determining that the condensation occurrence condition is met. The warning signal may contain an indication of the location of possible condensation occurrence. The method may comprise transmitting the warning signal to an monitoring device.

The method may comprise activating one or more devices arranged to mitigate the occurrence of condensation in the aspirating detection system, in response to determining that the condensation occurrence condition is met. For example, the method may comprise controlling, or more preferably decreasing, a speed of an aspirating device of the aspirating detection system. In another example, the method may comprise activating a heater arranged to heat the sample air from the monitored environment, wherein the heater is located proximate a boundary of the monitored environment.

The aspirating detection system may be an aspirating detection system according to the first aspect (optionally including one or more or all of the optional features of the first aspect).

The method of the second aspect may be a method of monitoring for condensation occurrence in an aspirating detection system according to the first aspect. Accordingly, the method of the second aspect may have one or more features corresponding to one or more or all of the optional features of the first aspect.

Viewed from a third aspect of the present invention, there is provided a computer-implemented method of designing an aspirating detection system for monitoring an environment. The method comprises: simulating operation of an aspirating detection system based on a plurality of predefined operating conditions, wherein the aspirating detection system comprises a sampling pipe in flow communication with a monitored environment and a central detection unit configured to draw the sample air along the sampling pipe; determining an ambient air temperature outside of the aspirating detection system and a corresponding sample air temperature inside the aspirating detection system for each of a plurality of flow locations along the sampling pipe and/or within the central detection unit based on the simulated operation; and if a temperature difference value between the ambient temperature and the sample air temperature exceeds a condensation threshold at a respective flow location, modifying a design of the aspirating detection system to incorporate a condensation mitigation device at the respective flow location.

By simulating operation of the aspirating detection system prior to installation and modifying the design of the aspirating detection system according to results of the simulation, aspirating detection systems installed according to the design may be better placed to mitigate the effects of condensation occurrence in aspirating detection systems.

The method may comprise creating an initial design of the aspirating detection system. The initial design may be based on one or more design factors, such as any one or more of the location of the monitored environment, the number or density of sampling locations required within the monitored environment, and the desired location of the central detection unit.

The initial design may provide an aspirating detection system generally comprising a central detection unit and a sampling pipe, although the aspirating detection system may include further features and/or components as desired. The sampling pipe should be at least partially exposed to the monitored environment.

The predefined operating conditions may include a range of temperatures for the monitored environment and a range of temperatures of the surrounding environment. The predefined operating conditions may comprise one or more operational speeds of an aspirating device of the aspirating detection system.

Simulating operation of the aspirating detection system may comprise simulation of steady-state operation of the aspirating detection system.

Simulating operation of the aspirating detection system may additionally or alternatively comprise simulation of one or more transient states of operation of the aspirating detection system. At least one of the one or more transient states may include conditions defining the introduction of warm air into a cooled monitored environment.

The plurality of flow locations may include one or more locations along the sampling pipe and/or within the central detection unit. One of the flow locations may correspond to a flow location disposed in a length of the sampling pipe located in the monitored environment. One of the flow locations may correspond to a flow location disposed in a length of the sampling pipe located outside of the monitored environment.

The method may comprise determining that condensation could occur at a location where the temperature difference value exceeds the condensation threshold at the respective flow location. Accordingly, modification of the of the design of the aspirating detection system may be based on identifying locations of possible condensation occurrence within the aspirating detection system.

The modification may comprise addition of a condensation mitigation device to the design. The condensation mitigation device may be added based on, e.g. at or proximate, the location of possible condensation occurrence. The condensation mitigation device may be a gravity-based water trap such as a U-shaped or water collection pipe; a heater; or the like.

Modifying the design of the aspirating detection system may accordingly comprise incorporating a gravity-based water trap at the respective flow location. Preferably, gravity-based water traps may be incorporated downstream of the monitored environment.

Modifying the design of the aspirating detection system may also comprise incorporating a heater at the respective flow location. Preferably, heaters may be incorporated proximate a boundary between environments, such as the monitored environment and an environment surrounding the central detection unit.

The method may comprise optimising placement of one or more temperature sensors for monitoring for condensation occurrence in the aspirating detection system based on the simulated operation.

Modifying the design of the aspirating detection system may comprise incorporating one or more temperature sensors for sensing a sample air temperature and/or an ambient air temperature outside of the aspirating detection system.

The method may be a computer-implemented method of designing an aspirating detection system according to the first aspect. Accordingly, the design for the aspirating detection system according to the third aspect may comprise one or more or all features according to the aspirating detection system of the first aspect. The method of the third aspect may incorporate and/or contemplate one or more features corresponding to one or more or all of the optional features of the first aspect.

Viewed from a fourth aspect, there is provided a method of installing an aspirating detection system for monitoring an environment. The method comprises: producing a design for the aspirating detection system according to a method as described in the third aspect; and installing the aspirating detection system according to the design.

The method of the fourth aspect may have one or more or all features (optionally including one or more or all features) of the third aspect.

BRIEF DESCRIPTION OF THE DRAWINGS

Certain exemplary embodiments of the invention are described below by way of example only and with reference to the accompanying drawings in which.

DETAILED DESCRIPTION

Figure 1:
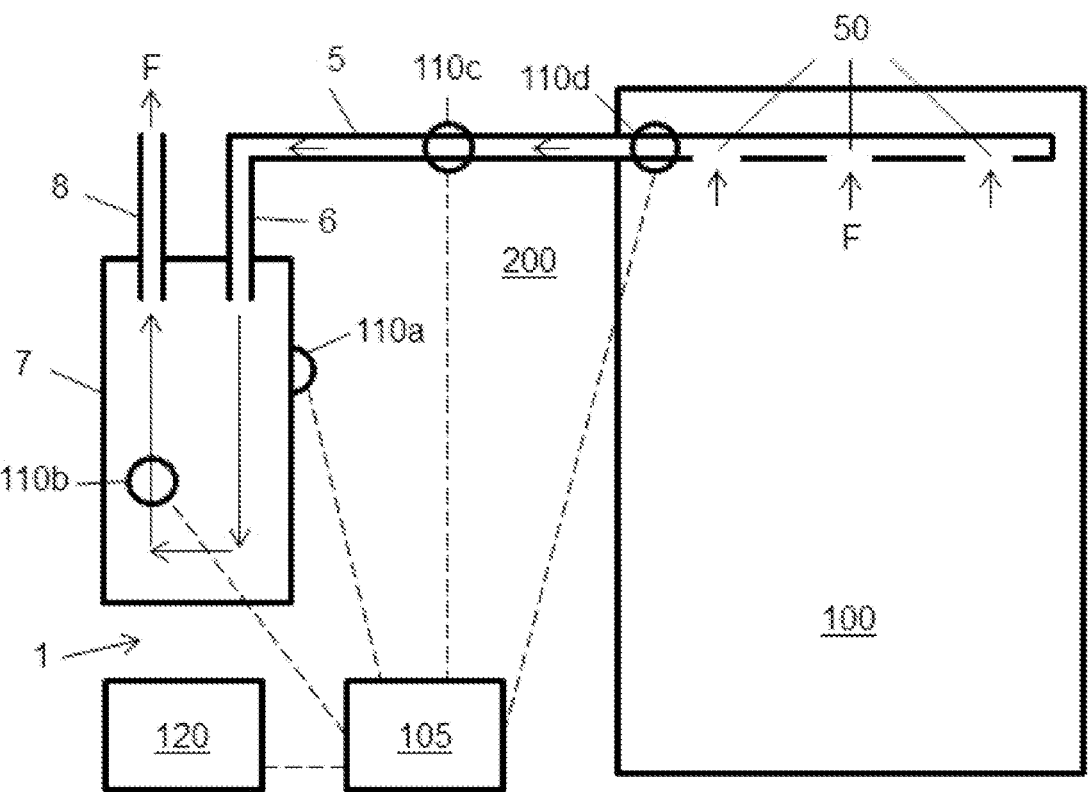
FIG. 1 schematically illustrates an aspirating detection system arranged to monitor an environment.

FIG. 1 shows a schematic illustration of an aspirating detection system 1 arranged to monitor an environment 100. The aspirating detection system 1 comprises a sampling pipe 5 which is partially disposed in the monitored environment 100, and a central detection unit 7 in flow communication with the sampling pipe 5. The sampling pipe 5 is partially exposed to the monitored environment 100 via a plurality of openings 50. Sample air is thereby able to flow in a flow direction F from the monitored environment 100 to the central detection unit 7 via the sampling pipe 5. Although a single sampling pipe 5 is illustrated, the sampling pipe 5 may represent, or be a part of, a broader network of pipes.

Figure 2:
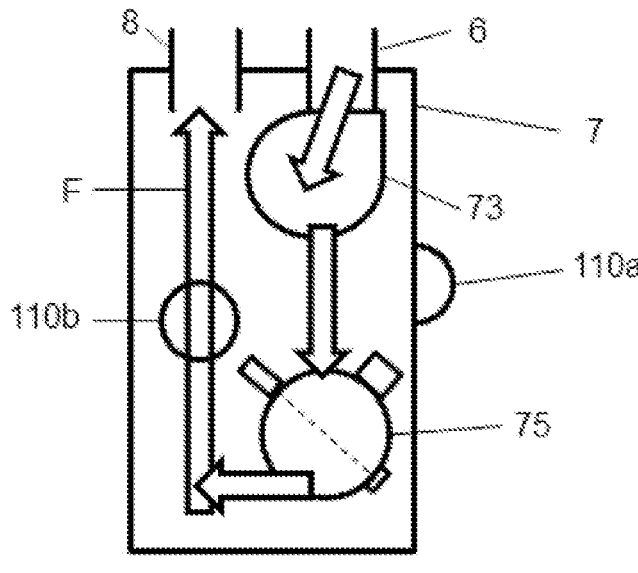
FIG. 2 shows a schematic representation of a central detection unit.

FIG. 2 shows a schematic cross-sectional view of the central detection unit 7. The central detection unit 7 comprises an inlet 6 through which sample air enters the central detection unit 7, and an outlet 8 through which sample air is exhausted from the central detection unit 7. The inlet 6 is connected to the sampling pipe 5. The direction of flow F of the sample air through the central detection unit 7 is represented via arrows.

The central detection unit 7 comprises an aspirating device 73. The aspirating device 73 is configured to draw air from the monitored environment 100 into the central detection unit 7 via the sampling pipe 5. In this regard, the aspirating device 73 generates a pressure differential across the aspirating detection system 1, from the plurality of openings 50 to the outlet 8. The aspirating device 73 thereby functions to actively sample air F from the monitored environment 100. The aspirating device 73 may be a pump, blower or a fan. The aspirating device 73 may comprise an impeller or the like.

The central detection unit 7 also comprises a detection device 75. The detection device 75 of the present embodiment is a smoke detection device 75, comprising a detection chamber, a light source, a light absorber and a light detector. The sample air is passed into the detection device 75 from the aspirating device 73 and through a beam of light emitted from the light source to the light absorber. If smoke particles are present in the sample air, the smoke particles scatter the light emitted by the light source. The detection chamber preferably comprises a mirrored surface which focuses the scattered light at the light detector. The presence of smoke particles can be determined according to the degree of scattering of the light emitted by the light source. By determining if smoke particles are present in the sample air, it can hence be determined if smoke indicative of e.g. a fire event is present in the monitored environment 100.

Although the detection device illustrated is a smoke detection device 75, the central detection unit 7 may comprise additional or alternative detection devices according to the desired purpose of the aspirating detection system 1.

In some embodiments, the monitored environment 100 is a refrigeration chamber or other refrigerated (i.e. actively cooled) environment. In the present embodiment the monitored environment 100 is configured to be maintained at approximately $-23°$ C. In other embodiments, the monitored environment 100 may be maintained at a temperature of less than $-5°$ C.; less than $-10°$ C.; less than $-15°$ C.; less than $-20°$ C.; or less than $-25°$ C.

Temperature differences across the aspirating detection system 1 can lead to the occurrence of condensation on surfaces of the internal and/or external surfaces of the sampling pipe 5 or the central detection unit 7. The flow F of sample air through the aspirating detection system 1 may cause the occurrence of condensation in the aspirating detection system 1 when the sample air contacts a surface or enters a region of the aspirating detection system 1 which is of significant temperature difference to the sample air.

For example, if the sample air is of a relatively low temperature, the sample air may cool the surfaces of the aspirating detection system 1 which may cause condensation on outer surfaces of the aspirating detection system 1. Alternatively, in situations where the sample air is of a high temperature relative to the regions of the aspirating detection system 1 and the sample air contacts a cold surface of the aspirating detection system 1, condensation may form on internal surfaces of the aspirating detection system 1.

In a further example, in the case of a refrigerated chamber as the monitored environment 100, the internal surfaces of the aspirating detection system 1 may be relatively cool due the temperature of the refrigerated sample air. However, when the refrigerated chamber is accessed, warm air may enter the chamber and be drawn into the aspirating detection system 1. The passage of this warm sample air through the cooled sampling pipes 5 may cause condensation on internal surfaces of the aspirating detection system 1. The formation of condensation may lead to ice build-up in regions of condensation. Further, the formation of condensation may result in water droplets interfering and/or damaging one or more components of the aspirating detection system 1.

To warn against the potential occurrence of condensation, the aspirating detection system 1 comprises a plurality of temperature sensors 110*a-d* distributed across the aspirating detection system 1. Each of the plurality of temperature sensors 110*a-d* are configured to monitor the temperature of the aspirating detection system 1 in the region in which they are disposed.

A first temperature sensor 110*a*, which can be described as an ambient temperature sensor, is arranged to measure an ambient temperature outside of the aspirating detection system 1. As illustrated in FIG. 1, part of the sampling pipe 5 and the entire central detection unit 7 are disposed in a surrounding environment 200. The ambient temperature monitored by the first temperature sensor 110*a* may therefore correspond to an average temperature of the surrounding environment 200.

A second temperature sensor 110*b*, which can be described as a sample air temperature sensor, is arrange to measure a temperature inside of the central detection unit 7 of the aspirating detection system 1.

The first temperature sensor 110*a* is not in flow communication with the sample air and thereby does not directly measure the sample air temperature. Preferably, the first temperature sensor 110*a* is located in a housing of the central detection unit 7. The first temperature sensor 110*a* may be located on an internal surface of the central detection unit or on an external surface of the central detection unit 7.

In some embodiments the ambient temperature, i.e. the temperature of the surrounding environment 200, may be unregulated. The ambient temperature of the surrounding environment 200 may vary seasonally. Alternatively, the surrounding environment may be located in a climate-controlled environment but may be maintained at room temperature, i.e. between 10 to 30° C.; between 15 to 25° C.; or between 19 to 23° C.

A second temperature sensor 110*b* is arranged to measure, or sense, a sample air temperature (i.e. an air flow temperature) of the aspirating detection system 1. The second temperature sensor 110*b* is disposed in the flow path F of the sample air to monitor the air flow temperature in the respective region in which the second temperature sensor 110*b-d* is located. Initially upon entering the sampling pipe 5 of the aspirating detection system 1, the sample air will have a temperature corresponding to the temperature of the monitored environment 100. Typically, the sampling pipe 5 is not insulated. Therefore, as the sample air travels through the sampling pipe 5, its temperature will deviate towards an equilibrium temperature, i.e. increase and/or decrease towards the ambient temperature of the surrounding environment 200.

As seen in FIG. 2, the second temperature sensor 110*b* may be located in the flow path F of the sample air through the central detection unit 7. The second temperature sensor 110*b* is thus disposed to directly monitor or sense the sample air temperature within the central detection unit 7.

Although the second temperature sensor 110*b* is located downstream of the detection device 75 as shown in FIG. 2, the second temperature sensor 110*b* may be located in the flow path F at any point within the central detection unit 7, provided it does not interfere with the operation and reliability of other components of the central detection unit 7 such as the aspirating device 73 or the detection device 75.

Optionally, additional temperature sensors, such as a third temperature sensor 100*c* and a fourth temperature sensor 100*d* may be located in the flow path F of the sample air along the sampling pipe 5. For example, the third temperature sensor 100*c* is located along a length the sampling pipe

5 outside of the monitored environment 100 and within the surrounding environment 100, and the fourth temperature sensor 100*d* is located along a length of the sampling pipe 5 within the monitored environment 100.

Whilst the third and fourth temperature sensors 110*c*, 110*d* are described in the present embodiment as being configured to monitor exclusively the sample air temperature, in some embodiments these temperature sensors 110*c*, 110*d* may be configured to additionally monitor an ambient temperature adjacent the respective temperature, i.e. a temperature of the surrounding environment 200 or the monitored environment 100, respectively. The third and fourth temperature sensors 110*c*, 110*d* may thus comprise at least two temperature sensing portions, sensors or probes configured to measure a sample air temperature and an ambient temperature at the respective location at which the temperature sensor 100*c*, 100*d* is disposed.

The third and fourth temperature sensors may each therefore act as both an ambient temperature sensor and a sample air temperature sensor.

Each of the temperature sensors 110*a*-*d* is in communication with a controller 105. The temperature sensors 110*a*-*d* are each in wireless communication with the controller 105, and communicate with the controller 105 using any suitable wireless communications protocol. In other embodiments, one or more of the temperature sensors 110*a*-*d* may instead be in wired communication with the controller 105.

The controller 105 receives a sensed ambient temperature value from the first temperature sensor 110*a* and also receives sensed sample air temperature values from the second to fourth temperature sensors 110*b*-*d*. From these values, the controller 105 determines a temperature difference value between the sensed ambient temperature value and each of the sensed sample air temperature values. The controller 105 then compares each of the temperature difference values with a temperature threshold value. A condensation occurrence condition, i.e. a condition for the likely occurrence of condensation, is considered to be met when the temperature difference value exceeds the temperature threshold value.

If the temperature difference value does not exceed the temperature threshold value, the controller 105 determines that an occurrence of condensation is unlikely. In other words, there is a negative determination of the condensation occurrence condition. In some embodiments, the controller 105 may be configured to take no particular action in response to the negative determination because this is the desired operational state of the aspirating detection system 1.

If the temperature difference value is found to exceed the temperature threshold value, the controller 105 determines that an occurrence of condensation is likely. In other words, there is a positive determination of the condensation occurrence condition.

In some embodiments, the controller 105 is configured to determine the region or location of possible condensation occurrence based on the location of the temperature sensors 110*a*-*d*. For example, each temperature sensor 110*a*-*d* may have an assigned or predetermined location. Taking the arrangement of temperatures sensors 110*a*-*d* shown in FIG. 1 and as described above, there may be three predetermined locations according to the placement of the second, third and fourth temperature sensors 110*b*-*d*.

If a temperature difference value associated with third or fourth temperature sensors 110*c* and 110*d* exceeds the temperature threshold value, but a temperature difference value associated with the second temperature sensor 110*b* does not exceed the temperature threshold value, the controller 105 may determine that an occurrence of condensation is likely along the sampling pipe 5 but not in the central detection unit 5.

In some embodiments, the temperature threshold value is a variable value. The controller 105 can be configured to calculate the temperature threshold value based on a temperature difference between the ambient temperature and its dew point. The dew point may be calculated based on an approximation of the average humidity, e.g. in a room or according to seasonal variations and the like. Alternatively, a humidity sensor may be used in the surrounding environment 200 to calculate the relative humidity.

In other embodiments, the temperature threshold value is a fixed value. For example, the temperature threshold value may be between 5 and 30° C.; between 10 and 25° C.; or between 15 and 20° C.

The controller 105 can take a number of actions in response to a positive determination of the condensation occurrence.

In some embodiments, the controller 105 is in communication with a display device 120. The display device 120 can be part of a device separate from the central detection unit 7, such as a fire control panel, a smartphone, a personal computer or the like. Alternatively, the display panel 120 may be integrated with the central detection unit 7. When the controller 105 determines that an occurrence of condensation is likely, the controller 105 sends a warning signal to the display device 120. The warning signal comprises an alert or information informing a user that condensation is likely occurring. The user can take action to maintain, or schedule maintenance, of the aspirating detection system 1 based on the warning signal. The warning signal can be configured to activate a visual or aural indicator to warn that the occurrence of condensation is likely.

The controller 105 can also be in communication with one or more devices which may be arranged to mitigate the occurrence of condensation in the aspirating detection system 1.

Figure 3:
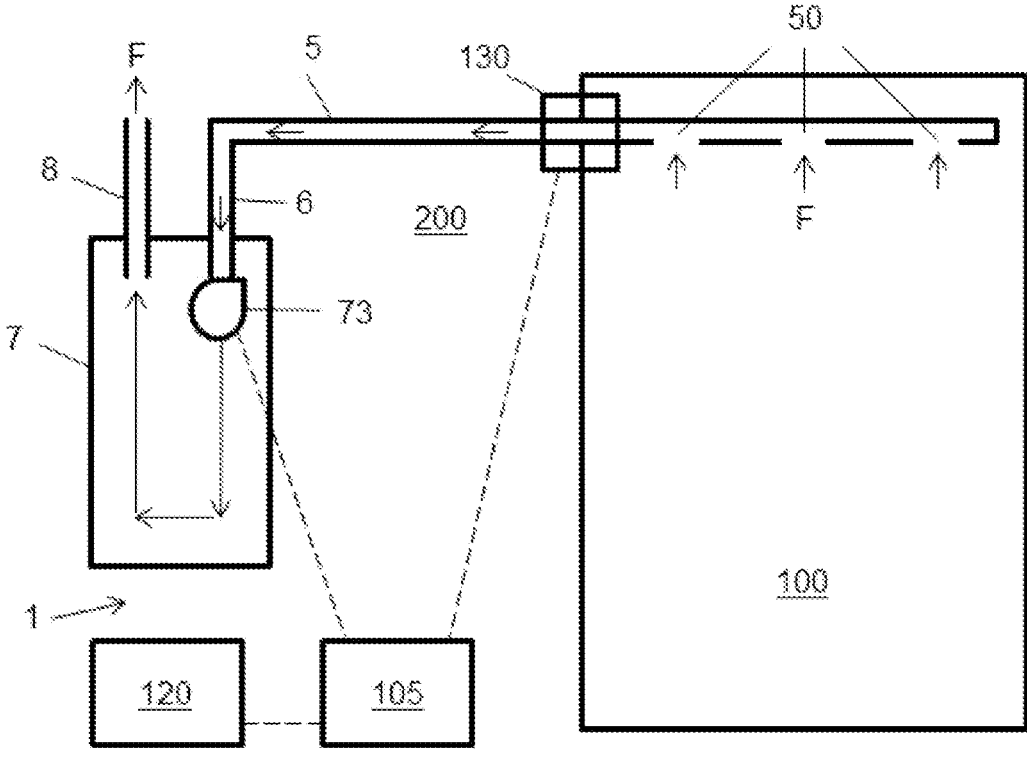
FIG. 3 schematically illustrates an aspirating detection system.

FIG. 3 shows a further schematic illustration of the aspirating detection system 1 of FIG. 1 including exemplary devices arranged to mitigate the occurrence of condensation. For reasons of clarity only, the temperature sensors 110*a*-*d* are omitted from FIG. 3.

In some embodiments, the controller 105 can be in wired and/or wireless communication with the aspirating device 73 and is operable to control the speed of the aspirating device 73. If the controller 105 determines that the temperature difference value exceeds the temperature threshold value, the controller 105 can decrease a speed of the aspirating device 73.

By decreasing the speed of the aspirating device 73, the flow volume of sample air is reduced. Where there is a reduced volumetric flow rate of sample air the sample air will reach ambient temperatures over a shorter distance. Accordingly decreasing the speed of the aspirating device 73 may reduce the temperature difference between the sample air and the aspirating detection system 1, thus reducing or mitigating the occurrence of condensation.

Decreasing the speed of the aspirating device 73 may decrease the sensitivity of the detection device 75. Therefore, the controller 105 may be configured to decrease the speed of the aspirating device 73 only when the temperature difference exceeds a temperature difference threshold. The temperature difference threshold is higher than the temperature threshold, such that the controller 105 only decreases the speed of the aspirating device 73 when the temperature difference value is much greater than the temperature threshold. Accordingly, the speed of the aspirating device 73 may only be decreased when the occurrence of condensation in or around the aspirating detection system 1 is highly probable.

The temperature difference threshold may be at least 3° C.; at least 5° C.; or at least 8° C. higher than the temperature threshold value.

In some embodiments, and as shown in FIG. 3, the controller 105 is also in communication with a heater 130. The heater 130 is arranged adjacent a boundary between the monitored environment 100 and the surrounding environment 200. The use of a heater 130 as a device to mitigate condensation is particularly effective when the monitored environment 100 is a cool environment, such as a refrigeration chamber or other actively cooled environment. The heater 130 can be selectively operated to heat the air sample from the monitored environment 100 as it passes via the sampling pipe 5 into the part of the aspirating detection system 1 disposed in the surrounding environment 200. The heater 130 heats the sample air from the monitored environment 100, thereby reducing the temperature difference between the sample air temperature and the ambient temperature.

The controller 105 is arranged to activate the heater 130 when the controller 105 determines that the temperature difference value exceeds the temperature threshold. More preferably, the controller 105 is arranged to activate the heater 130 when the ambient temperature exceeds the sample air temperature by a difference value greater than the temperature threshold.

By activating the heater 130 when the temperature difference exceeds the temperature threshold rather than e.g. constantly, the rate of energy consumption of the heater 130 may be improved via its intermittent operation whilst also mitigating the occurrence of condensation in the aspirating detection system 1.

Figure 4:
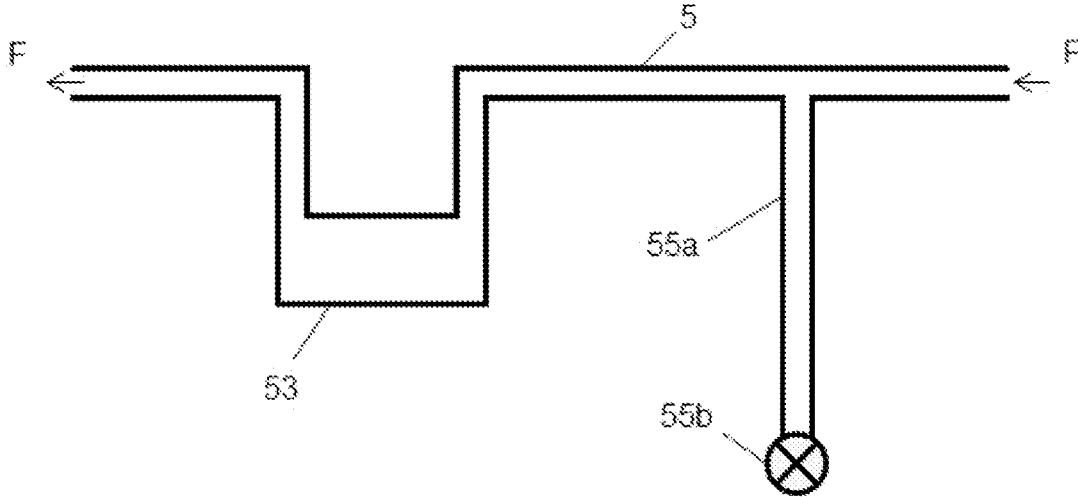
FIG. 4 shows a schematic representation of a section of a sampling pipe of an aspirating detection system.

FIG. 4 schematically represents a section of the sampling pipe 5 of the aspirating detection system 1. The illustrated section sits between the monitored environment 100 and the central detection unit 7. The direction of airflow F illustrated in FIG. 4 is hence from the monitored environment 100 to the central detection unit 7 (i.e. along the sampling pipe 5 as illustrated in FIG. 1).

FIG. 4 shows two water traps 53, 55 in flow communication with the sampling pipe 5. The water traps 53, 55 are arranged to collect condensed water at a singular location of the sampling pipe 5. In this respect, each of the water traps 53, 55 as illustrated and described herein are gravity-based water traps although alternative arrangements are also envisaged. The water traps 53, 55 provide known locations or regions where condensed water collects for ease of maintenance of the aspirating detection system 1 and may also prevent the further ingress of condensation downstream of the water traps 53, 55.

As illustrated in the downstream portion of the sampling pipe 5, there is provided a U-bend 53. The U-bend 53 provides a U-shaped flow path in the sampling pipe 5 with an enlarged volume at the bottom of the U-shaped flow path (as defined with respect to gravity). Condensation may collect in the enlarged volume whilst still facilitating a flow of air through the U-bend 53.

As illustrated in the upstream portion of the sampling pipe 5, there is provided a water pipe 55. The water pipe 55 comprises a pipe 55a and a valve 55b. To evacuate the water pipe 55a, the valve 55b may be actuated. The pipe 55 descends from the sampling pipe 5, and does not provide a complete flow path for the sample air. Instead, the water pipe

55 provides a gravity-based collection point for condensation that may form in the sampling pipe 5.

In some embodiments and as described above, the controller 105 is configured to determine the region or location of possible condensation occurrence based on the location of the temperature sensors 110a-d. An operator of the system may then determine that condensation mitigation devices should be placed at the determined region of condensation occurrence. The operator of may then retroactively modify the aspiration detection system 1 such that it can better mitigate the occurrence of condensation.

For example, if the controller 105 determines that a condensation occurrence is likely at a location where there is no dedicated condensation mitigation device or where there is likely a greater temperature difference with increased frequency and/or duration, it may be desirable to install a condensation mitigation device at that location.

Additionally, the techniques described may be employed at a design stage prior to installation of the aspirating detection system 1. For example, the operation of a planned aspirating detection system 1 may be simulated to determine locations where condensation may occur, and suitable modification may be made to the design to incorporate one or more condensation mitigation devices.

First, a design of an aspirating detection system 1 is created. This may be created by any conventional means, taking into account necessary factors such as the location of the monitored environment 100, the number or density of sampling locations required within the monitored environment 100 and the desired location of the central detection unit 7.

Next, a set of operating conditions are determined. The operating conditions include a range of temperatures for the monitored environment 100, a range of temperatures of the surrounding environment 200, and operational speeds of the aspirating device 73 of the central detection unit 7. Where there are multiple monitored environments 100 or surrounding environments 200, a range of temperatures is determined for each such environment.

Operation of an aspirating detection system 1 according to the design is then simulated based on the plurality of predefined operating conditions. This may be simulated using any appropriate simulation technique.

Optionally, the simulation may comprise simulation of steady-state operation of the aspirating detection system 1, as well as simulation of one or more transient states of operation of the aspirating detection system 1, such as warm air being introduced into a cooled monitored environment.

Based on the simulation, a simulated ambient air temperature outside of the simulated aspirating detection system 1 and a corresponding simulated sample air temperature inside the simulated aspirating detection system 1 is determined at each of a plurality of flow locations. For example, the flow location may include one or more locations along the sampling pipe and/or within the central detection unit 7. These could, for example, correspond to the locations of the temperature sensors 110a-d shown in FIG. 1.

If a temperature difference between the simulated ambient temperature and the simulated sample air temperature exceeds a condensation threshold at a respective flow location, then it may be determined that condensation could occur at that location were the design to be implemented.

In response to determining a location of possible condensation, the design of the aspirating detection system 1 may be modified to include a condensation mitigation device at or proximate the location of possible condensation. The modified design may then be re-simulated in the same manner described above, and optionally further modifications may be made to the design if condensation locations are still identified.

Once a design has been finalised, it may be supplied to an installer to install an aspirating detection system 1 in accordance with the design.

The invention claimed is:

1. An aspirating detection system for monitoring an environment, the aspirating detection system comprising:

a central detection unit configured to analyze sample air from the monitored environment;

a sampling pipe for providing the sample air to the central detection unit from the monitored environment, wherein the central detection unit is configured to draw the sample air along the sampling pipe;

at least one ambient temperature sensor configured to sense an ambient temperature value corresponding to an ambient temperature outside of the aspirating detection system;

at least one sample air temperature sensor configured to sense a sample air temperature value corresponding to a temperature of the sample air; and a controller configured to determine a condensation occurrence condition is met when a difference between the sample air temperature value and a corresponding ambient temperature value exceeds a condensation threshold value;

the controller is configured to decrease a speed of an aspirating device of the central detection unit in response to determining that the condensation occurrence condition is met.

2. An aspirating detection system as claimed in claim 1, wherein the at least one ambient temperature sensor includes a first temperature sensor located in a housing of the central detection unit.

3. An aspirating detection system as claimed in claim 1, wherein the at least one sample air temperature sensor includes a second temperature sensor located in a flow path of the sample air through the central detection unit.

4. An aspirating detection system as claimed in claim 1, wherein the at least one sample air temperature sensor includes one or more temperature sensors located in a flow path of the sample air along the sampling pipe.

5. An aspirating detection system as claimed in claim 4, wherein the at least one ambient air temperature includes the one or more temperature sensors located in a flow path of the sample air along the sampling pipe.

6. An aspirating detection system as claimed in claim 4, wherein the one or more temperature sensors includes a third temperature sensor located along a length of the sampling pipe outside of the monitored environment.

7. An aspirating detection system as claimed in claim 4, wherein the one or more temperature sensors includes a fourth temperature sensor located along a length of the sampling pipe within the monitored environment.

8. An aspirating detection system as claimed in claim 1, wherein the controller is configured to determine a location of possible condensation occurrence based on a location of where the sample air temperature value was sensed.

9. An aspirating detection system as claimed in claim 1, wherein the controller is configured to generate a warning signal in response to determining that the condensation occurrence condition is met;

wherein the controller is configured to transmit the warning signal to a monitoring device.

10. An aspirating detection system as claimed in claim 1, wherein the controller is configured to generate a warning signal in response to determining that the condensation occurrence condition is met;

wherein the warning signal comprises a command to activate an indicator.

11. An aspirating detection system as claimed in claim 1, comprising a heater located proximate a boundary of the monitored environment and arranged to heat the sample air from the monitored environment;

wherein the controller is configured to activate the heater in response to determining that the condensation occurrence condition is met.

12. A method of monitoring for condensation occurrence in an aspirating detection system as claimed in claim 1, the method comprising:

sensing an ambient temperature value corresponding to an ambient temperature outside of the aspirating detection system;

sensing a sample air temperature value corresponding to a temperature of sample air inside the aspirating detection system; and determining a condensation occurrence condition is met when a difference between the sample air temperature value and a corresponding ambient temperature value exceeds a condensation threshold value.

13. A method as claimed in 12, the method comprising:

determining a location of possible condensation occurrence based on a location of where the sample air temperature value was sensed; and generating a signal in response to determining that the condensation occurrence condition is met, the signal containing an indication of the location of possible condensation occurrence; and transmitting the signal to a monitoring device comprising a display device, wherein the monitoring device displays the signal for user.

* * * * *